(12) United States Patent
Marik

(10) Patent No.: US 8,690,878 B2
(45) Date of Patent: Apr. 8, 2014

(54) FLEXIBLE ANCHOR EXTENDERS

(75) Inventor: Greg C Marik, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 294 days.

(21) Appl. No.: 13/083,773

(22) Filed: Apr. 11, 2011

(65) Prior Publication Data

US 2012/0259374 A1    Oct. 11, 2012

(51) Int. Cl.
   *A61B 17/70*    (2006.01)
(52) U.S. Cl.
   USPC ........................................ 606/86 A; 606/246
(58) Field of Classification Search
   CPC ....................................................... A61B 17/70
   USPC .................. 606/246, 264–272, 86 A, 99, 104
   See application file for complete search history.

(56) References Cited

U.S. PATENT DOCUMENTS

| | | |
|---|---|---|
| 7,465,306 B2 | 12/2008 | Pond, Jr. et al. |
| 7,491,208 B2 | 2/2009 | Pond, Jr. et al. |
| 2005/0277934 A1 | 12/2005 | Vardiman |
| 2006/0247658 A1 | 11/2006 | Pond, Jr. et al. |
| 2006/0264934 A1 | 11/2006 | Fallin |
| 2006/0271050 A1 | 11/2006 | Piza Vallespir |
| 2007/0233079 A1 | 10/2007 | Fallin et al. |
| 2008/0077139 A1 | 3/2008 | Landry et al. |
| 2008/0125817 A1 | 5/2008 | Arnett et al. |
| 2008/0140132 A1 | 6/2008 | Perez-Cruet |
| 2008/0233079 A1 | 9/2008 | Chang et al. |
| 2008/0269805 A1 | 10/2008 | Dekutoski et al. |
| 2009/0088803 A1 | 4/2009 | Justis et al. |
| 2009/0099605 A1 | 4/2009 | Fallin et al. |
| 2009/0171391 A1 | 7/2009 | Hutton et al. |
| 2009/0326586 A1 | 12/2009 | Duarte |
| 2010/0030283 A1 | 2/2010 | King et al. |
| 2010/0036443 A1 | 2/2010 | Hutton et al. |

*Primary Examiner* — Pedro Philogene
*Assistant Examiner* — David Comstock

(57) ABSTRACT

There is disclosed a system for positioning a connecting element adjacent one or more bones or bony portions, such as the spinal column, through a minimally invasive surgical approach. The system generally includes at least one bone anchor engageable to the one or more bones or bony portions and at least one anchor extender removably engaged to the bone anchor. A connecting element is movable along a longitudinal axis of the anchor extender. In response to movement of the connecting element along the longitudinal axis toward the bone anchor, the anchor extender flexes, bends or otherwise reconfigures to allow a leading end of the connecting element to be rotated away from the longitudinal axis so that the connecting element can be positioned in a transverse orientation to the longitudinal axis along the one or more bones or bony portions at a location adjacent the bone anchor.

17 Claims, 5 Drawing Sheets

FLEXIBLE ANCHOR EXTENDERS

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. However, there remains a need for further improvements in instruments, systems and methods for stabilizing bony structures using minimally invasive techniques.

SUMMARY

One nonlimiting embodiment of the present application is directed to a system for positioning a connecting element adjacent one or more bones or bony portions, such as the spinal column, through a minimally invasive surgical approach. The system generally includes at least one bone anchor engageable to the one or more bones or bony portions and at least one anchor extender removably engaged to the bone anchor. A connecting element inserter instrument is engageable with a connecting element to move the connecting element along a longitudinal axis of the anchor extender. In response to movement of the connecting element along the longitudinal axis toward the bone anchor, the anchor extender flexes, bends or otherwise reconfigures to a axially non-linear configuration allow a leading end of the connecting element to be rotated away from the longitudinal axis so that the connecting element is positioned along the one or more bones or bony portions at a location adjacent the bone anchor. However, in other embodiments, different forms and applications are envisioned.

For example, another embodiment of the subject application is directed to a system for minimally invasive surgery that includes at least one bone anchor including a distal bone engaging portion and a proximal receiving portion. The system also includes at least one anchor extender extending along a longitudinal axis between a proximal end portion and a distal end portion configured to releasably engage with the at least one bone anchor. The at least one anchor extender includes a passage extending between its proximal and distal end portions. An elongated connecting element is positionable through the passage of the at least one extender and is movable along the longitudinal axis of the at least one anchor extender from the proximal end portion toward the distal end portion. The at least one anchor extender bends, flexes or otherwise reconfigures to an axially non-linear configuration to accommodate placement of the connecting element into the passage. The axially non-linear configuration also changes to accommodate the connecting element moving distally along the longitudinal axis of the at least one anchor extender and to allow the connecting element to be manipulated to orient the connecting element in a substantially transverse orientation to the longitudinal axis as the connecting element exits the distal end portion of the at least one anchor extender.

In yet another embodiment, a system for minimally invasive surgery includes a first bone anchor and a second bone anchor. Each of the first and second bone anchors includes a distal bone engaging portion and a proximal receiving portion. The system also includes a first anchor extender extending along a longitudinal axis between a proximal end portion and a distal end portion configured to releasably engage with the first bone anchor. A second anchor extender extends along a longitudinal axis between a proximal end portion and a distal end portion that is configured to releasably engage with the second bone anchor. At least one of the anchor extenders includes a passage extending between its proximal and distal end portions. An elongated connecting element is positionable through the passage of the at least one extender and is movable along the longitudinal axis of the at least one anchor extender from the proximal end portion toward the distal end portion. The at least one anchor extender bends, flexes or otherwise reconfigures to allow the connecting element to be moved distally along the longitudinal axis of the at least one anchor extender and to allow the connecting element to be manipulated to orient the connecting element in a substantially transverse orientation to the longitudinal axis as the connecting element exits the distal end portion of the at least one anchor extender for placement of the leading end of the connecting element into engagement with the bone anchor engaged to the other anchor extender.

Another embodiment of the present application is a unique system for minimally invasive surgery in a patient. Other embodiments include unique methods, systems, devices, kits, assemblies, equipment, and/or apparatus involving minimally invasive surgical systems and techniques.

Further embodiments, forms, features, aspects, benefits, objects and advantages of the present application shall become apparent from the detailed description and figures provided herewith.

DESCRIPTION OF THE ILLUSTRATED EMBODIMENTS

Figure 1:
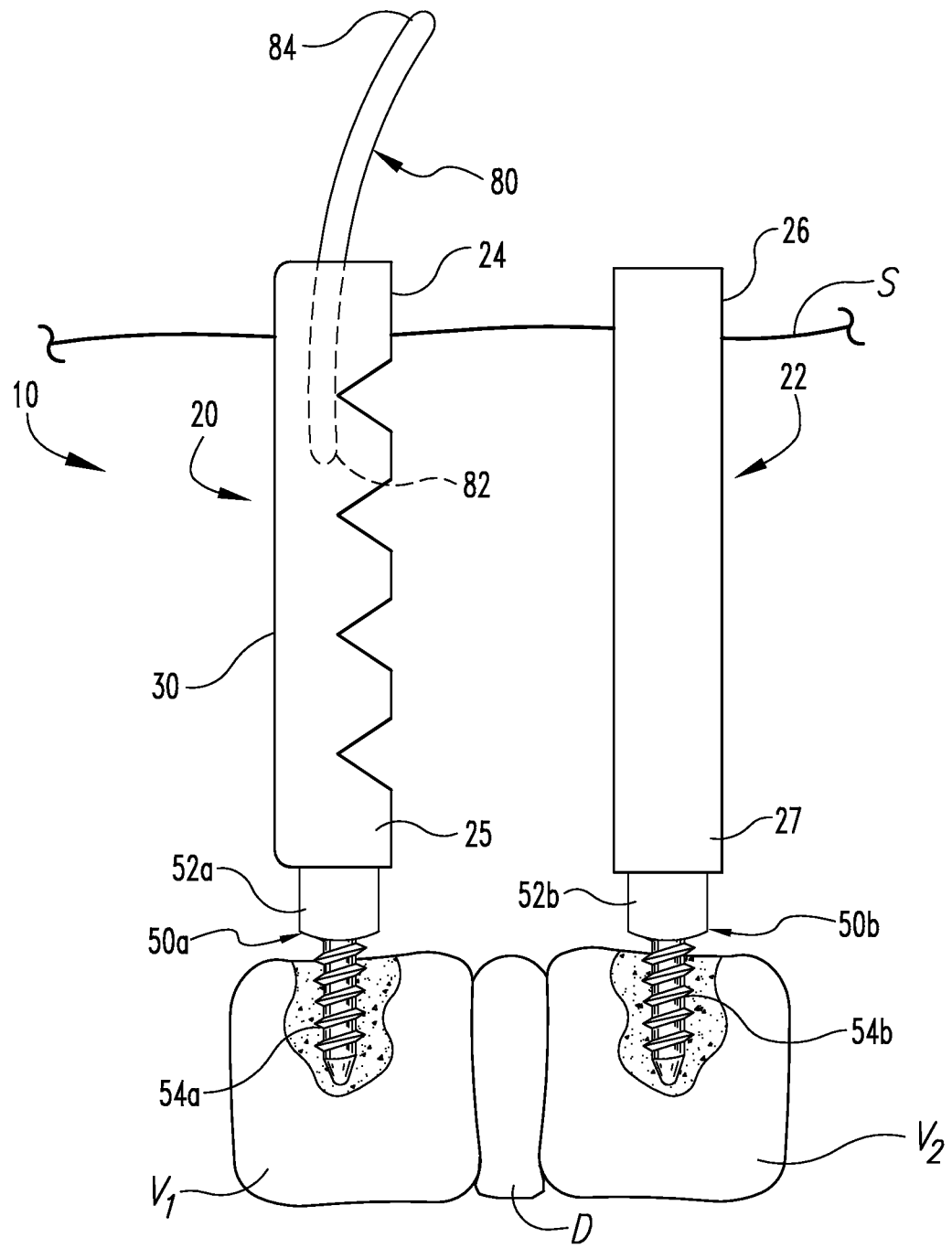
FIG. 1 is a side elevation view of a system for positioning a connecting element in a patient in minimally invasive surgical procedures.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

The subject application is generally directed to systems for positioning a connecting element adjacent one or more bones or bony portions, such as the spinal column, through a minimally invasive surgical approach. The systems generally include a number of bone anchors engageable to the one or more bones or bony portions and a number of anchor extenders removably engaged to the bone anchors. A connecting element is positionable into at least one of the anchor extenders and is movable along a longitudinal axis of the anchor extender toward the bone anchor. In response to movement of the connecting element along the longitudinal axis toward the bone anchor, the at least one anchor extender bends, flexes, or otherwise deforms from its initial, axially linear configuration to allow a non-linear connecting element to pass through the anchor extender and/or to allow a leading end of the connecting element to be rotated away from the longitudinal axis for positioning at a location adjacent the number of bone anchors. In one aspect of this arrangement, the anchor extender assumes axially non-linear configurations to allow the connecting element to pass through the anchor extender and to be introduced to the location adjacent the number of bone anchors through the same incision through tissue and muscle in which the anchor extender is positioned. In addition, applications in non-minimally invasive surgeries are also contemplated.

Figure 2A:
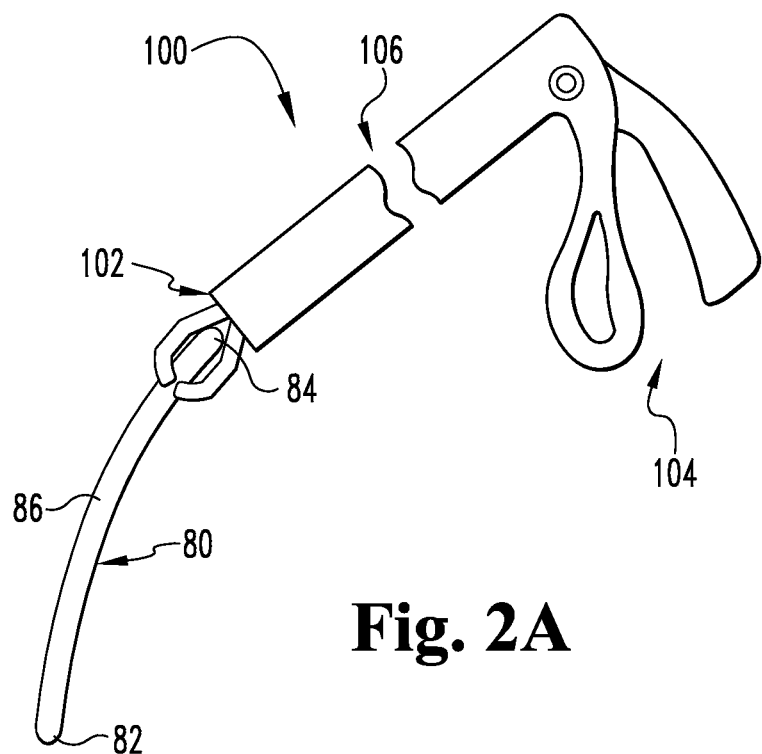
FIG. 2A is a perspective view of a connecting element engaged to an inserter instrument.

Referring now to FIG. 1, there is shown a minimally invasive surgical system 10 that is positioned relative to a portion of the spinal column including adjacent vertebrae $V_1$, $V_2$ and a disc D positioned therebetween. It should be appreciated that use of system 10 in connection with more than two adjacent vertebrae or even at other anatomical locations besides the spinal column are also contemplated. System 10 includes two anchor extenders 20, 22 releasably mountable to respective ones of anchors 50a, 50b and a connecting element 80. An inserter instrument 100, such as shown in FIG. 2A, may also be provided to hold and position connecting element 80 during insertion and implantation. In other non-illustrated forms, system 10 may include one or more anchors and/or anchor extenders in addition to anchors 50a, 50b and anchor extenders 20, 22.

Anchors 50a, 50b include proximal receiving portions 52a, 52b configured to receive connecting element 80 and a distal bone engaging portion 54a, 54b. In the illustrated embodiment, bone engaging portions 54a, 54b are bone screws with a threaded shank to engage the bony structure of the underlying vertebrae $V_1$, $V_2$. Proximal receiving portions 52a, 52b are receivers having a pair of opposing arms defining a longitudinal passage. The arms further define a proximally/distally extending opening that opens at a proximal end of the arms to receive an engaging member (not shown), such as a set screw, cap, nut, or other engaging member to secure connecting element 80 in the passage of receiving portion 52a, 52b. Bone engaging portions 54a, 54b can be pivotally received in proximal receiving portions 52a, 52b through the distal openings thereof, and structured to interact therewith to provide anchors 50a, 50b with multi-axial capabilities that permit either a selected number of positions or infinitely numbered of positions of bone engaging portions 54a, 54b relative to proximal receiving portions 52a, 52b.

Other forms for anchors 50a, 50b are contemplated, including uni-axial and uni-planar forms. The bone engaging portion can also be in the form of a spike, staple, hook, fusion device, cannulated screw, fenestrated screw, interbody device, intrabody device, clamp, plate, suture anchor, bolt, pin or other bone engaging member. The receiving portion can be in the form of a saddle, yoke, eye-bolt or through-hole, side opening member, bottom opening member, top-opening member, eyelet, or any other structure engageable to connecting element 80.

Figure 2B:
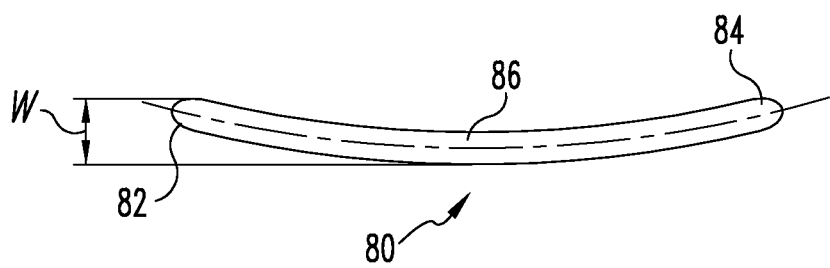
FIG. 2B is an elevation view of one embodiment connecting element.

In the illustrated embodiment, as shown in FIG. 2B, connecting element 80 is a rigid rod curved with an elongated body 86 extending along an arc between its leading end 82 and trailing end 84. The curvature of connecting element 80 defines a maximum overall width W created by the offset of ends 82, 84 from the central portion of body 86. However, it is contemplated that connecting element 80 can have a curvature that varies or is compounded along its length, or could be linear. In addition, in other forms it is contemplated that connecting element 80 can include any configuration known for a rod, implant, or fastener, so long as connecting element 80 is insertable using anchor extender 20 to guide its insertion in order to stabilize adjacent vertebrae $V_1$, $V_2$. Further, it is contemplated that connecting element 80 can be non-rigid, elastic and/or super-elastic and in the form of a cable, band, wire, or artificial ligament that is used in tethering, guiding, or other surgical procedures. The connecting element can include one or more acute bends and variable arcs. For non-rigid connecting elements, a rigid carrier can be provided to which connecting element 80 is mounted for insertion through anchor extender 20 as discussed further below.

In the illustrated form of system 10, anchor extender 22 is configured the same as anchor extender 20. However, in other forms, it is contemplated that anchor extender 22 could be configured differently than anchor extender 20 so long as it facilitates engagement of anchor 50b to the bony structure. Anchor extender 22 can be a tube, shaft, screwdriver, or post. Non-limiting examples of alternative configurations for anchor extender 22 may be found in U.S. Pat. Nos. 6,530,929, 7,497,869 and 7,520,879 and in U.S. Patent Publication Nos. 2005/0171540 and 2008/0319477, just to provide a few possibilities.

Figure 6:
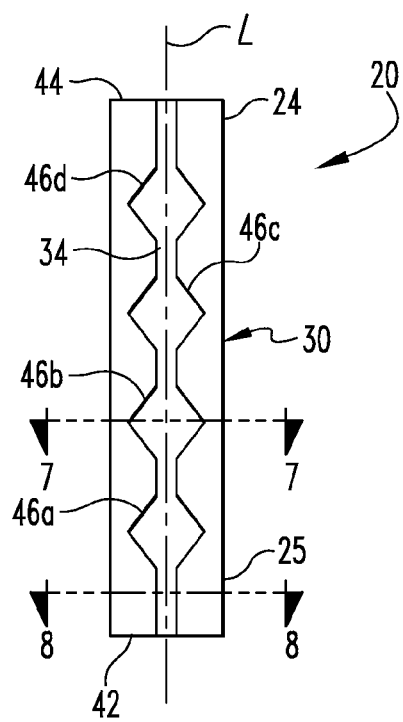
FIG. 6 is an elevation view of an anchor extender of the system of FIG. 1.
Figure 7:
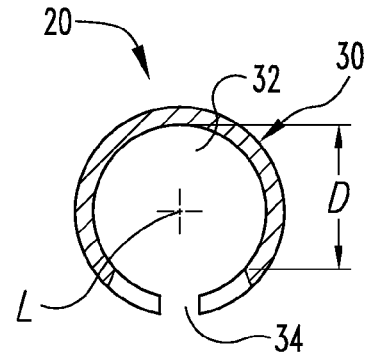
FIG. 7 is a section view along view line 7-7 of FIG. 6.
Figure 8:
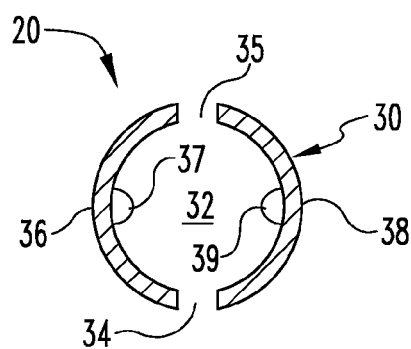
FIG. 8 is a section view along line 8-8 of FIG. 6.

Anchor extender 20 includes an initial configuration that extends linearly along a longitudinal axis L between a proximal end portion 24 and a distal end portion 25 configured to releasably engage with anchor 50a. Similarly, anchor extender 22 also extends between a proximal end portion 26 and a distal end portion 27 configured to releasably engage with anchor 50b. Further details regarding anchor extender 20 are described below in connection with FIGS. 6-8. Anchor extender 20 generally includes an elongated body 30 extending along and centered on longitudinal axis L in its axially linear configuration. Body 30 defines a passage 32 centered on longitudinal axis L that extends between and opens at proximal end portion 24 and distal end portion 25. Body 30 also defines at least one side opening 34 that faces anchor extension 22 and anchor 50b when implanted. Side opening 34 extends from the distal end 42 of body 30 proximally along at least a portion of the length of body 30. In one embodiment, side opening 34 extends along the entire length of body 30 from its distal end 42 to its proximal end 44. In another embodiment, side opening 34 extends along about one half the length of body 30 from its distal end 42 toward its proximal end 44. In still another embodiment, side opening 34 extends along about less than one-fourth of the length of body 30 from its distal end 42 toward its proximal end 44.

Distal end portion 25 of anchor extender 20 is configured to releasably engage proximal receiving portion 52a of anchor 50a. In the illustrated embodiment, distal end portion 25 is divided into a pair of engaging members 36, 38 positioned on opposite sides of body 30 that are separated by side opening 34 and an opposite slot 35. Engaging member 36, 38 can flex outwardly to allow placement of receiving portion 52a therebetween, and are resilient to engage the sides of receiving portion 52a. Engaging members 36, 38 may include a projection, nub or other member 37, 39, respectively, received in a recess in the outer side of a respective adjacent part of receiving portion 52a, 52b to axially secure anchor extender 20 to receiving portion 52a. In still another embodiment, distal end portion includes an internal lip arrangement that is secured beneath flanges at the proximal end of receiving portion 52a. Other embodiments contemplate a bayonet lock, threaded attachment, fasteners, or other suitable engagement relationship to secure anchor extender 20 to receiving portion 52a. In yet another embodiment, anchor extender 20 is joined with receiving portion 52a during manufacture to provide a one-piece member. A break-off joint is provided between anchor extender 20 at receiving portion 52a that provides a location in which the anchor extender 20 is removed upon application of sufficient tension and/or shearing forces.

Referring back to FIGS. 1-5, use of system 10 to insert connecting element 80 for implantation in a patient will be described. In FIG. 1, anchor extenders 20, 22 are mounted to corresponding anchors 50a, 50b engaged to vertebrae V1, V2, respectively. Anchor extenders 20, 22 can be installed through a small incision or puncture in skin S simultaneously with anchors 50a, 50b, or positioned through the incision of puncture for mounting distal portions 25, 27 to already installed anchors. In any event, at least anchor extender 20 forms or defines a pathway for insertion of connecting element 80 into the patient. As discussed below, system 10 allows insertion of connecting element 80 to a location that connects anchors 50a, 50b without requiring any additional incisions or punctures other than those used to accommodate placement of anchors 50a, 50b and anchor extenders 20, 22.

Figure 3:
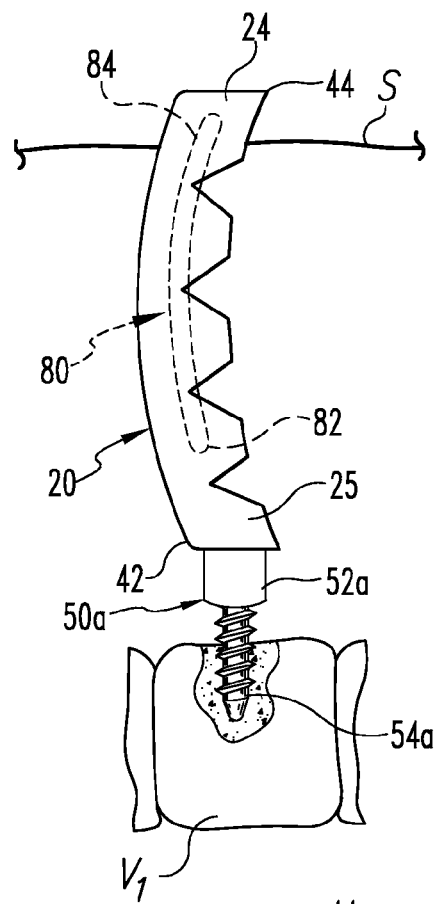
FIG. 3 is an elevation view of a portion of the system of FIG. 1 showing the connecting element positioned in an anchor extender.

In order to hold connecting element 80 during insertion, an inserter instrument such as inserter instrument 100 can be provided to releasably engage connecting element 80. One example of inserter instrument 100 is shown in FIG. 2A, although it should be appreciated that any suitable inserter instrument can be used. Inserter instrument 100 includes a grasping portion 102 and a handle actuating portion 104 connected thereto with shaft portion 106. The user can grasp handle actuating portion 104 and operate it to manipulate grasping portion 102 to releasably hold connecting element 80 thereto. In the illustrated embodiment, connecting element 80 extends generally axially from the longitudinal axis of shaft portion 106 so that grasping portion 102 is engaged to trailing end 84 of connecting element 80. This allows leading end 82 of connecting element 80 to be first inserted into passage 30 and guided along longitudinal axis L of anchor extender 20, as shown in FIG. 3.

Figure 4:
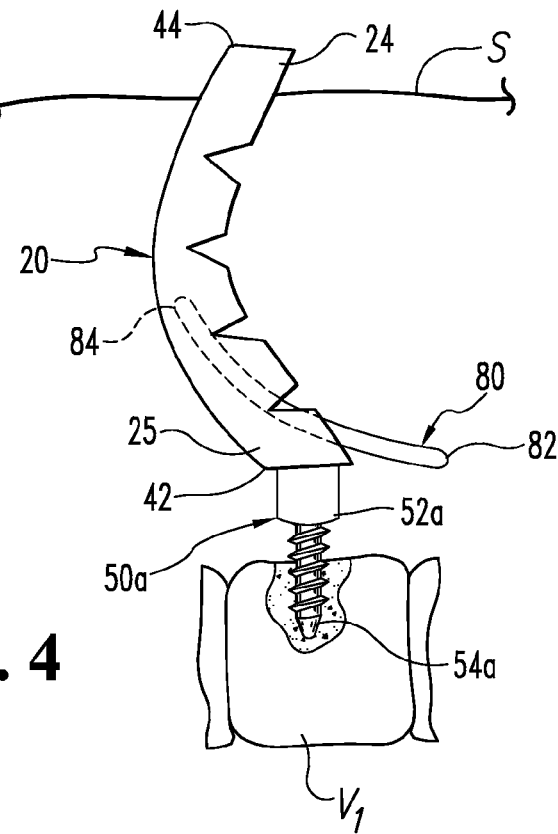
FIG. 4 is an elevation view of the portion of the system of FIG. 3 showing the connecting element exiting the anchor extender.
Figure 5:
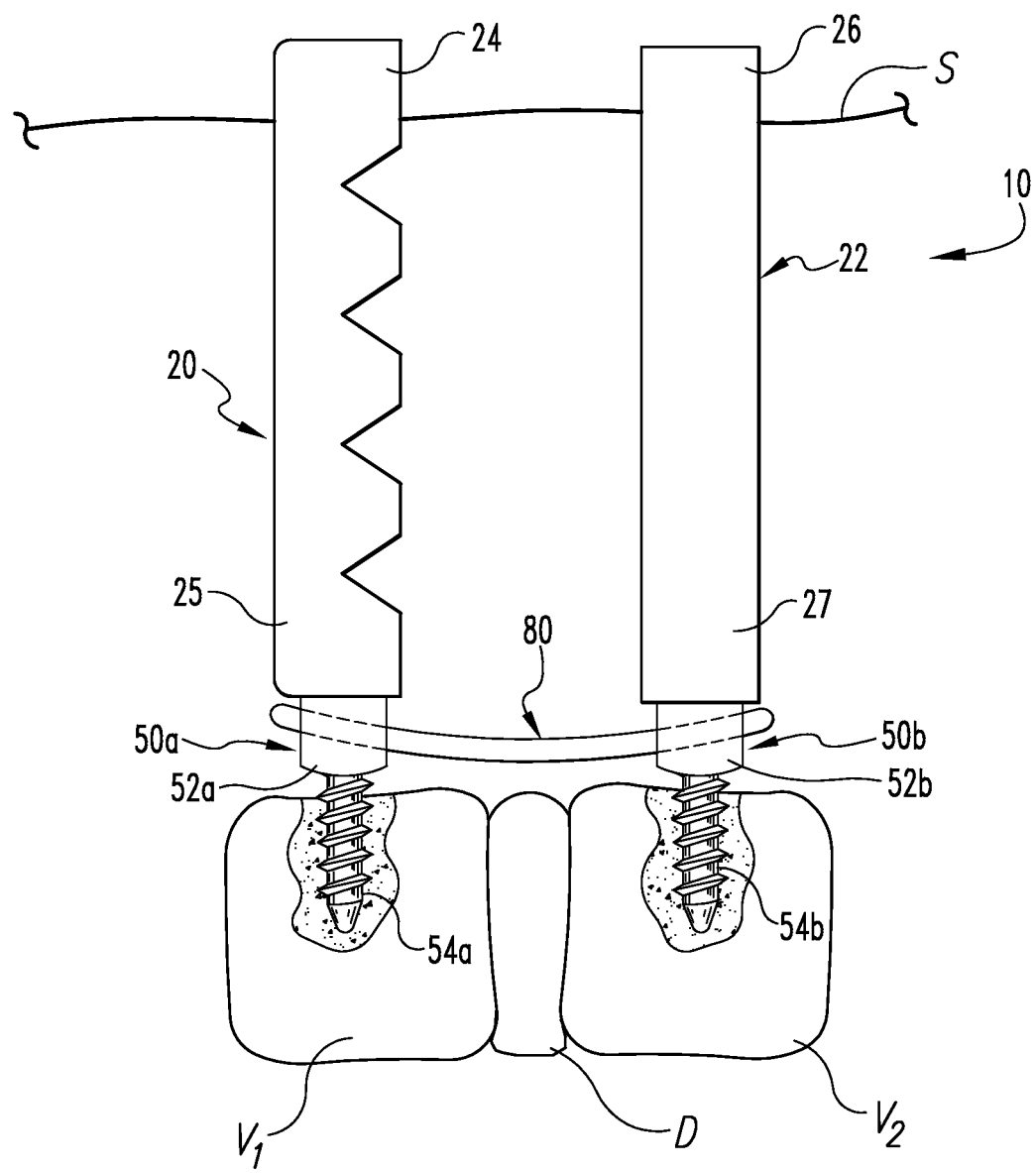
FIG. 5 is a side elevation view of the system of FIG. 1 showing the connecting element extending between first and second bone anchors.

In the illustrated embodiment, connecting element 80 includes a curved configuration extending between leading end 82 and trailing end 84 such that, when positioned axially in anchor extender 20, the cross-sectional dimension D of passage 30 may not be sufficient to accommodate the width W of connecting element 80. Therefore, as shown in FIG. 3, body 30 of anchor extender 20 flexes to provide a non-linear axial configuration so that all or a substantially portion of the length of connecting element 80 can be received in passage 32. In the illustrated embodiment, body 30 flexes so that its central portion located between ends 42, 44 bows away from anchor extender 22 while ends 42, 44 remain in their pre-insertion position. Connecting element 80 can be further advanced distally along anchor extender 20 and pivoted to a substantially transverse orientation to longitudinal axis L so that leading end 82 exits anchor extender 22 through side opening 34 at distal portion 25, as shown in FIG. 4. If necessary, anchor extender 20 further bows away from anchor extender 22 to provide additional non-linear axial configurations to allow connecting element 80 to be pivoted in passage 30 so that leading end 82 extends toward anchor 50b mounted to anchor extender 22. Connecting element 80 is advanced further into anchor extender 20 until trailing end 84 is positioned in receiving portion 52a of anchor 50a and leading end 82 is positioned in receiving portion 52b of anchor 50b, as shown in FIG. 5. Anchor extender 20 can be resilient so that once connecting element 80 passes therethrough it returns to or toward it non-bowed, axially linear, pre-insertion configuration.

Once connecting element 80 is positioned in receiving portions 52a, 52b of anchors 50a, 50b, an engaging member, such as a set screw, nut, cap or other suitable member can be engaged to receiving portions 52a, 52b to secure connecting element 80 to anchors 50a, 50b. Anchor extenders 20, 22 provide a pathway for guiding positioning of the engaging member through the skin and tissue of the patient to the respective anchor 50a, 50b. Furthermore, anchor extenders 20, 22 can be manipulated to compress or distract vertebrae V1, V2, or to displace or rotate one of vertebrae V1, V2 relative to the other to provide the desired alignment therebetween before connecting element 80 is finally secured to anchors 50a, 50b.

Anchor extender 20 includes a stiffness profile on at least one side thereof that allows flexing of body 30 between ends 42, 44 in response to the forces present during manual insertion of connecting element 20 through passage 32. In the illustrated embodiment, body 30 includes a series of reliefs 46a, 46b, 46c, 46d along its length on a first side of body 30 that provide areas of material reduction in body 30, allowing body 30 to be compressed or reduced in length along its first side to accommodate the curvature of connecting element 80 and the pivoting of connecting element 80 in passage 32. Furthermore, in the illustrated embodiment, reliefs 46a-46d are formed by triangular notches having bases orientated toward the first side of body 30, and slot 34 extends through and interconnects reliefs 46a-46d to further reduce material along the first side of body 30. In other embodiments, slot 34 does not interconnect or extend through all or a portion of reliefs 46a-46d. While triangular notches provide an efficient reduction of material while retaining structural integrity, in still other embodiments reliefs 46a-46d can be rectangular, square, oval, circular, irregular, or include any suitable configuration that provides a stiffness profile that allows flexing, bending and bowing of body 30 to accommodate insertion of connecting element 80 into passage 32 and manipulation of connecting element 80 in passage 32.

In still other embodiments, reliefs are provided on the second side of body 30 opposite its first side, either in addition to or in lieu of reliefs 46a-46d. In yet other embodiments, the reduced stiffness profile of body 30 is formed by fabricating body 30 from a flexible material, or with a mesh structure that allows flexing of body 30. The body 30 can be solid and made from flexible material with or without openings. Body 30 can also be configured with overlapping sections that are shingled or telescoped relative to one another that can allow body 30 to articulate to accommodate the geometry of the connecting element. Such overlapping sections would prevent soft tissue from entering any apertures that may be created along the body to enhance flexibility. Adjacent sections of the flexible body 30 can be connected with one another via a hinged connection. In addition, flexible body 30 can be connected to the bone anchor with a hinged connection, allowing the flexible body 30 to pivot to orient its distal end toward the bone anchor to facilitate placement of the connecting element from the distal end toward the other bone anchor.

In one embodiment, systems for positioning a connecting element adjacent the spinal column in minimally invasive surgical procedures include one or more extenders removably engaged to one or more anchors engaged to a bony segment. The anchor extenders provide a reference to the respective anchor locations within the patient even when the anchor is obstructed by skin and/or tissue of the patient. Similarly, the anchor extenders are sized such that a portion thereof extends above the skin of a patient when they are engaged to the bone anchors. In one form, it is contemplated that separate incisions may be made for using and positioning each anchor and anchor extender. An inserter instrument is engageable with a connecting element to move the connecting along a longitudinal axis of one of the anchor extenders. In response to movement of the connecting element along the longitudinal axis toward the bone anchor, the anchor extender flexes, bends or otherwise deforms to an axial non-linear configuration allow passage of a non-linear connecting element therethrough and/or allow a leading end of the connecting element to be rotated away from the longitudinal axis until the connecting element is positioned at a location adjacent each of the number of bone anchors. The system herein provides at least one extender for insertion of a connecting element into a patient to interconnect a plurality of bone anchors by creating a pathway from the skin to at least one of the anchors that is non-linear and that alters in shape to ensure that the connecting element is placed to the anchor engaged to the at least one extender and manipulatable within the patient to extend from the at least one anchor extender to the one or more additional anchors. Still, it should be appreciated that alternative forms, aspects, configurations, arrangements and methods are contemplated with respect to the subject matter disclosed and described herein.

Alternative configurations of the systems described herein are also contemplated. For example, in one or more forms the systems described herein can be configured to insert a connecting element that extends across and is engaged to anchors positioned at three or more vertebral levels or to three or more bony portions or segments. In addition, use of the systems described herein for stabilization of bones, bony structures or other anatomical features besides vertebral stabilization are contemplated. Furthermore, the systems and instrumentation described herein may also be used in surgical procedures involving animals, or in demonstrations for training, education, marketing, sales and/or advertising purposes. In addition, the systems and instrumentation described herein may be also used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A system for minimally invasive surgery, comprising:
a connecting element including an elongated body extending between a leading end and an opposite trailing end;
at least one bone anchor including a distal bone engaging portion and a proximal receiving portion comprising spaced apart arms defining a channel for receiving the trailing end of the connecting element; and
at least one anchor extender with an elongated tubular body extending in a linear axial configuration along a longitudinal axis between a proximal end portion and a distal end portion configured to releasably engage with said arms such that said distal end portion extends between said arms, said tubular body defining a passage between said proximal and distal end portions, wherein said tubular body defines a stiffness profile that allows said tubular body to bend to a non-linear axial configuration between said distal and proximal end portions in response to advancement of said connecting element into said passage along said longitudinal axis and in response to changes of orientations of said connecting element relative to said longitudinal axis while said connecting element is located in said passage.

2. The system of claim 1, wherein said connecting element is curved along an arc between said leading end and said trailing end and so that a mid-portion of said elongated body is offset from said leading and trailing ends.

3. The system of claim 2, wherein said offset between said mid-portion and said leading and trailing ends of said connecting element defines a maximum width that is greater than a maximum cross-sectional dimension of said passage of said tubular body.

4. The system of claim 2, wherein said tubular body includes a slot extending through a first side of said tubular body along at least said distal end portion of said tubular body, wherein said slot is sized to allow said connecting element to pass therethrough.

5. The system of claim 4, wherein said slot extends from said proximal end portion to said distal end portion of said tubular body.

6. The system of claim 5, wherein said slot interconnects and extends through a series of reliefs along said first side that reduces said stiffness profile of said tubular body on said first side.

7. The system of claim 6, wherein said reliefs include a triangular shape having a base oriented toward said first side.

8. The system of claim 5, wherein said tubular body includes a second slot along said distal end portion that is located on a second side of said tubular body opposite of said first side.

9. The system of claim 8, wherein said slots divide said distal end portion into first and second engaging members that are removably engageable to opposite sides of said proximal receiving portion of said bone anchor.

10. The system of claim 1, wherein said tubular body has a C-shaped cross-sectional configuration.

11. The system of claim 1, wherein said distal end portion extends continuously between said arms.

12. A system for minimally invasive surgery, comprising:
a first bone anchor and a second bone anchor, each of said first and second bone anchors including a distal bone engaging portion and a proximal receiving portion comprising spaced apart arms;
a connecting element including an elongated body extending between a leading end and an opposite trailing end, wherein said connecting element includes a length between said leading end and said trailing end sized for said connecting element to be engaged to said proximal receiving portions of said first and second bone anchors when said first and second bone anchors are engaged to respective ones of first and second vertebrae;
a first anchor extender extending along a longitudinal axis between a proximal end portion and a distal end portion configured to releasably engage with said arms of said first bone anchor such that said distal end portion extends between said arms;
a second anchor extender extending along a longitudinal axis between a proximal end portion and a distal end portion configured to releasably engage with said proximal receiving portion of said second bone anchor; and
wherein at least one of said first and second anchor extenders includes a tubular body that defines a passage between said proximal and distal end portions thereof extending in a linear axial configuration, wherein said tubular body includes a series of reliefs between said proximal and distal end portions that allows said tubular body to be manipulated to a non-linear axial configuration between said distal and proximal end portions in response to insertion of said connecting element into said passage, thereby allowing said connecting element to be advanced from said proximal end portion through said distal end portion of said at least one of said first and second anchor extenders to the proximal receiving portion of the bone anchor releasably engaged to the other of said first and second anchor extenders.

13. The system of claim 12, wherein said at least one said first and second anchor extenders bends away from the other of said first and second anchor extenders in said non-linear axial configuration in response to advancement of said connecting element into said passage along said longitudinal axis and in response to changes of orientations of said connecting element relative to said longitudinal axis while said connecting element is located in said passage.

14. The system of claim 13, wherein said tubular body flexes to permit said leading end of said connecting element to be rotated away from said longitudinal axis and through an opening in a first side of said at least one of said first and second anchor extenders that faces the other of said first and second anchor extenders.

15. The system of claim 12, wherein said distal end portion of said at least one of said first and second anchor extenders includes a first slot extending through a first side thereof and a slot extending through a second side thereof opposite said first side, said first and second slots dividing said distal end portion into a pair of engaging members for releasably engaging opposite sides of said proximal receiving portion of said respective one of said first and second bone anchors.

16. The system of claim 12, wherein said connecting element is curved along an arc between said leading end and said trailing end so that a mid-portion of said elongated body is offset from said leading and trailing ends.

17. The system of claim 16, wherein said offset between said mid-portion and said leading and trailing ends of said connecting element defines a maximum width that is greater than a maximum cross-sectional dimension of said passage of said tubular body.

* * * * *